United States Patent [19]

Demarcq et al.

[11] 4,029,722
[45] June 14, 1977

[54] POLYFLUOROALKYL GLYCOL MONOESTERS OF ORTHOPHOSPHORIC ACID, AND THEIR SALTS AND METHOD OF PREPARATION

[75] Inventors: Michel Démarcq; Joseph Sleziona, both of Lyon, France

[73] Assignee: Produits Chimiques Ugine Kuhlmann, Paris, France

[22] Filed: Apr. 19, 1974

[21] Appl. No.: 462,549

[30] Foreign Application Priority Data

Apr. 19, 1973 France .............................. 73.14313

[52] U.S. Cl. ............................ 260/953; 260/246 B; 260/293.9; 260/429.9; 260/435 R; 260/448 R; 260/924; 260/937; 260/955; 260/968; 260/983

[51] Int. Cl.² ............................................ C07F 9/09

[58] Field of Search .......... 260/953, 968, 983, 924, 260/429.9, 435 R, 448 R, 246, 293.9

[56] References Cited

UNITED STATES PATENTS

| | | | |
|---|---|---|---|
| 2,559,754 | 7/1951 | Bittles et al. | 260/955 |
| 3,083,224 | 3/1963 | Brace et al. | 260/955 |
| 3,407,248 | 10/1968 | Klauke et al. | 260/953 X |

OTHER PUBLICATIONS

Janzen et al., Canadian Journal of Chemistry, vol. 48, July 1970, pp. 1987–1990.

*Primary Examiner*—Richard L. Raymond
*Attorney, Agent, or Firm*—Pennie & Edmonds

[57] ABSTRACT

New monoesters of phosphoric acid with polyfluorinated glycols having the formulas

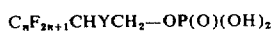

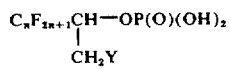

wherein Y is hydroxyl, can be prepared by alkaline saponification of the corresponding compounds wherein Y is chlorine. The new diacid monoesters and their salts are effective surfactants, unexpectedly stable in alkaline media.

10 Claims, No Drawings

POLYFLUOROALKYL GLYCOL MONOESTERS OF ORTHOPHOSPHORIC ACID, AND THEIR SALTS AND METHOD OF PREPARATION

BACKGROUND OF THE INVENTION

1. Field of the Invention

The present invention relates to new compounds which are monoesters of phosphoric acid with polyfluorinated glycols having the formula $C_nF_{2n+1}$—CHOH—$CH_2OH$ wherein $C_nF_{2n+1}$ designates a perfluorinated alkyl having $n$ equal to an integer from 2 to 18, the term monoester including both the straight-chain alpha ester

and the branched-chain best ester having the formula

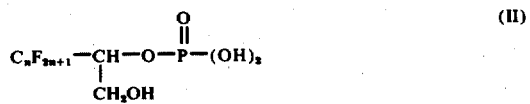

and also mixtures of these monoesters in all proportions.

The invention relates also to salts of these monoesters and their mixtures.

DESCRIPTION OF THE PRIOR ART

Phosphorus compounds having polyfluorinated alkyl moieties have been the subject of much research. Those which are sufficiently polar, in particular those whose molecules terminate in a diacid phosphate group —$OPO_3H_2$, optionally neutralized by a base, are valued for their surface activity and for the hydrophobic and oleophobic properties which they confer upon textile materials plastics, leather, waxes and the like.

Phosphorus compounds having polyfluorinated chains are used, for example, as emulsifying agents in general or particularly in the emulsion polymerization of fluorinated olefins (U.S. Pat. Nos. 2,559,754 and 2,676, 985); as levelling agents or stain-resisting agents; in polishing waxes, in particular in emulsified products conferring finishes of high brilliance (U.S. Pat. No. 3,083,224 and French Pat. No. 1,454,535); or as additives to chromium plating baths (U.S. Pat. No. 3,194,840.)

Among the known phosphorus compounds having polyfluorinated groups, there can also be cited phosphonic acids of the formula $C_nF_{2n+1}$ (—$CH_2$)$_m$—$PO_3H_2$ (French Pat. No. 1,454,535) and H—$C_nF_{2n}$—$PO_3H_2$ (U.S. Pat. No. 2,559,754) and the partial phosphate esters of the formula [$C_nF_{2n+1}$ ($CH_2$)m O]$_y$ PO(OH)$_{3-y}$ (U.S. Pat. No. 3,083,224) patents which have been started in trade literature to be related to the commercial product ZONYL S·13 marketed by DuPont de Nemours.

Other phosphorus compounds having polyfluorinated chains are utilized as lubricants or additives to lubricants, including, for example, neutral phosphoric esters of the type ($C_nF_{2n+}$—$CH_2O$)$_3$PO (U.S. Pat. No. 2,888,481), esters of polyfluorophosphonates such as H($CF_2$)$_n$ ($CH_2$)$_3$—PO($OCH_3$)$_2$ (French Pat. No. 1,453,535) and the esters of polyfluorinated alcohols with benzene phosphonic acid (U.S. Pat. No. 3,337,665).

Analogous compounds are used as hydraulic fluids; thus there are disclosed phosphoric esters of polyfluorinated alcohols (U.S. Pat. Nos. 2,754,317 and 2,754,318), phosphonic esters of polyfluorinated alcohols (U.S. Pat. No. 3,246,030), phosphonic esters of polyfluoroalkylphenols (French Patent 1,430,849), phosphoramidates of polyfluorinated alcohols (French Pat. No. 1,450,918) and esters of N-polyfluoroalkyl phosphoramidic acids. (Belgian Pat. No. 672,659)

Present applicants are also applicants of Ser. No. 206,512 filed in the U.S. Pat. Office December 19, 1971 and corresponding to French application No. 70/44,290, which covers phosphate esters of perfluoroalkylchlorohydrins and their corresponding acid chlorides. Thus, there are disclosed the straight-chain alpha isomer

and the branched-chain beta isomer

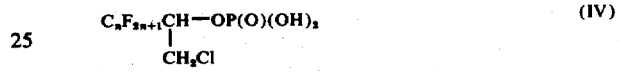

Compounds III can also be designated as mono (2-chloro-2 perfluoroalkyl-ethyl) dihydrogen phosphate whereas compounds IV can also be designated as mono (2-chloro-1-perfluoroalkylethyl) dihydrogen phosphate.

Said corresponding acid chlorides were disclosed in the aforementioned Ser. No. 206,512 to have the respective structures

and

SUMMARY OF THE INVENTION

Present applicants have now established that when either esters III and IV or esters V and VI are treated with a saponifying base, the main product obtained by the hydrolysis or saponification comprises corresponding phosphate esters in which the chlorines on the alkyl moiety have been replaced by hydroxyls. Surprisingly, even though the phosphate ester is an ester of the strong acid phosphoric acid and esters of strong acid are in general easily hydrolyzable, the amount of saponifying attack at the phosphate ester linkage is exceeding small, even negligible, and the product of saponification contains in largest amount phosphate esters corresponding to formulas I and II.

The new compounds I and II have proved to be very effective as surface active agents, being surprisingly stable in alkaline medium, and providing a new range of hydrophilic-lipophilic balance favoring the hydrophilic in greater degree than the corresponding starting esters III and IV. Although applicants do not wish to be bound by theoretical considerations, it seems reasonable to attribute this shift in the surfactant balance to the greater polarity resulting from the replacement of chlorine atoms by hydroxyl, thus increasing the solubility of the phosphate end of the molecule in aqueous solvents and in polar solvents in general.

The presence of the hydroxyl groups in the esters of this invention furthermore provides a reactive site for optional additional modification of the molecules with functional groups such as, exemplarily, sulfato, phosphato or poly(ethyleneoxy) groups or polymerizable moieties such as acryloxy or methacryloxy groups.

According to the previous disclosure in the above mentioned Ser. No. 206,512, present applicats have shown that compounds III and IV are produced from the corresponding chlorophosphates V and VI by hydrolysis in plain water, as exemplarily by boiling. Consequently, applicants have further established that when starting with these acids chlorides to make the hydroxylated monophosphates of the instant invention, it is not necessary to effect preliminary isolation of the chloroalkyl esters III and IV. The acid chlorides V and VI and simply submitted directly to a basic saponification.

In short, the present invention comprises an acid product and its salts, said acid product containing at least one monoester of a perfluoroalkyl glycol having the formula

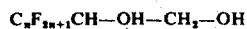
$C_nF_{2n+1}CH-OH-CH_2-OH$ with phosphoric acid, which monoester is a straight-chain alpha isomer

$$C_nF_{2n+1}CHOHCH_2-OP(O)(OH)_2 \qquad (I)$$

on the branched-chain beta isomer

$$\begin{array}{l}C_nF_{2n+1}CHO-P(O)(OH)_2 \\ \phantom{C_nF_{2n+1}}| \\ \phantom{C_nF_{2n+1}}CH_2-OH\end{array} \qquad (II)$$

wherein $C_nF_{2n+1}$ designates a perlfuorinated alkyl and wherein $n$ is an integer from 2 to 18.

The present invention also comprises a process for preparing said product which comprises saponifying at least one phosphoric monoester of a $C_2$–$C_{18}$-perfluoroalkyl ethylene chlorohydrin, which monoester is a straight-chain alpha isomer

$$\begin{array}{l}\phantom{C_nF_{2n+1}CHCl-}O \\ \phantom{C_nF_{2n+1}CHCl-}\| \\ C_nF_{2n+1}CHCl-CH_2OP=X_2\end{array} \qquad \text{III or V}$$

or a branched-chain beta isomer

$$\begin{array}{l}\phantom{C_nF_{2n+1}}O \\ \phantom{C_nF_{2n+1}}\| \\ C_nF_{2n+1}CHO-P=X_2 \\ \phantom{C_nF_{2n+1}}| \\ \phantom{C_nF_{2n+1}}CH_2Cl\end{array} \qquad \text{IV or VI}$$

wherein X can be OH or Cl, and wherein again $n$ is an integer from 2 to 18.

The new compounds I and II can be designated as perfluoroalkyl glycol monoesters of orthophosphoric acid, or more specifically as, respectively, mono (2-hydroxy-2 perfluoroalkylethyl) dihydrogen phosphate and mono (2-hydroxy-1-perfluoroalkylethyl) dihydrogen phosphate.

DETAILED DESCRIPTION

The basic saponification of this invention can take place in aqueous medium, alcoholic medium or in a water-soluble solvent inert to strong bases. As saponifying base, there is used a mineral base such as alkali-metal hydroxides including sodium, potassium, lithium, cesium and rubidium hydroxides; basic salts such as sodium carbonate, potassium carbonate, sodium bicarbonate, potassium bicarbonate; any sodium borate, exemplarily borax; ammonia or an amine, particularly tertiary amines such as trimethylamine, triethylamine, N-methyl-morpholine, triethanolamine, triisopropanolamine, dimethylethanolamine and the like; and quaternary ammonium hydroxides such as tetramethyl ammonium hydroxide, N,N-dimethyl, N,N-diethyl ammonium hydroxide, monomethyl triethanolammonium hydroxide and the like.

The preferred basic saponification agents are sodium hydroxide and potassium hydroxide.

When starting with a diacid monoester III and/or IV, the quantity of base used can be from 1 to 6 equivalents per atom of phosphorus, the preferred quantity being from 2.5 to 3.5 equivalents. When starting with a chlorophosphate V and/or VI, the quantity of base used can be from 3 to 8 equivalents per phosphorus atom, the preferred quantity being from 4.5 to 5.5 equivalents.

The compounds III, IV, V, and VI which are used as starting compounds in the preparative method of this invention are new compounds which are the subject of present Applicant's copending application, Ser. No. 206,512. The perfluorinated alkyl group which is common to all of these substances can be any straight-chain or branched alkyl having from 2 to 18 carbon atoms and having substantially all of its hydrogens replaced by fluorine. Exemplarily, said alkyl group can be pentafluoroethyl, heptafluoroisopropyl, nonafluoro-n-butyl, nonafluoro-isobutyl, nonafluoro-secondary butyl, nonafluoro-tertiary butyl, undecafluoro-n-amyl, undecafluoro-isoamyl, undecafluoro-tertiary amyl, tridecafluoro-n-hexyl, undecafluoro cyclohexyl, pentadecafluoroheptyl, heptadecafluoro octyl, nonadecafluorononyl, perfluorinated decyl ($C_{10}F_{21}$), perfluorinated undecyl ($C_{11}F_{23}$), perfluorinated lauryl ($C_{12}F_{25}$), perfluorinated myristyl ($C_{14}F_{29}$), perfluorinated tridecyl ($C_{13}F_{27}$), perfluorinated pentadecyl ($C_{15}F_{31}$), perfluorinated cetyl ($C_{16}F_{33}$), perfluorinated heptadecyl ($C_{17}F_{35}$), perfluorinated stearyl ($C_{18}F_{37}$) and the like.

The temperature at which the saponification is carried out can be selected from the range −20° to +200° C; the pressure can be equal to or greater than atmospheric pressure. It is preferred to operate at atmospheric pressure, or at a pressure slightly higher than atmospheric, exemplarily up to about 30 psig, at a temperature in the range +20° to +120° C.

It should be noted that the relative amounts of straight and branched isomers are not necessarily maintained during the course of the basic saponification of this invention. For example, if the starting product is the branched isomer as in IV or VI, the saponified product will not in general be composed uniquely of the corresponding branched beta-monoester II but, on the contrary, will usually be a mixture of the alpha-monoesters I and II, even such a mixture in which the straight-chain alpha ester is predominant.

These facts were not predictable before the present invention. Although Applicants do not wish to be limited by theoretical considerations, a reasonable explanation for these surprising results is that the nucleophilic displacement of the chlorine in molecule IV takes place not by direct attack of a hydroxyl ion but by intramolecular reaction of the phosphate ion to form a diester of the $R_f$-substituted glycol which has the structure of a dioxaphospholane cycle; this cyclic diester intermediate is capable of being hydrolyzed in two possible directions, thus:

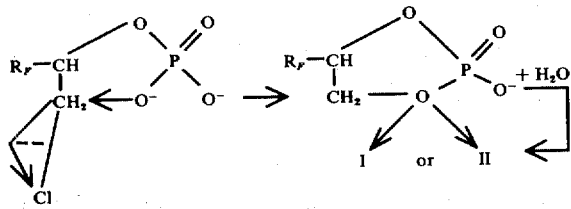

This reaction scheme would seen to be confirmed by the presence of said cyclic diester intermediate among the secondary products of saponification. (See Example 1, below.)

The salts of the diacid monoesters I and II which are likewise an object of this invention, comprise more particularly the salts of the alkali and alkaline-earth metals, of aluminum, zinc and lead, also salts formed by reaction of the acid with ammonia or amines, and the quaternary ammonium salts. Salts can be prepared from the diacid by conventional procedures of neutralization by a base, as is well known by those skilled in the art. Such neutralization can be partial, resulting in various mixtures of acid and salts having a range of pH and related properties suitable for particular end uses. Additional amounts of other salts can also be added to the partially or totally neutralized composition for the purpose of "building" certain properties such as wetting or surface tension.

It is also possible to prepare salts of the diacids of this invention, either pure or in mixtures with other salts, directly in the solution in which the basic saponification has taken place, optionally with special adjustment of pH. Thus the solution containing chloride salts from the saponification optionally containing also additional salts added as above described, can simply be evaporated to leave a dried product. Or, the desired salt can be insolubilzed by the addition of a suitably selected non-electrolyte. Or, an electrolyte possessing a common ion can be added to "salt out" the desired product. Or, again, a double decomposition can be affected to precipitate a salt having a different cation.

The products of the present invention, including the dihydrogen mono(polyfluoromonohydroxyalkyl) phosphates and also their miscellaneous salts, have numerous applications as wetting agents, emulsifying agents and foaming agents, particularly in basic media; as levelling agents or as stain-resistant agents in emulsion paints such as latex paints and in emulsion or latex polishes for floors and for furniture; as corrosion inhibitors, retarders of solvent evaporation and in general as hydrophobic and oleophobic agents.

The invention will be further illustrated by description in connection with the following specific examples of the practice of it, the proportions here and elsewhere herein being expressed as parts by weight unless specifically stated to the contrary.

EXAMPLE 1

As starting product, a chlorinated monoester $C_6F_{13}CH(CH_2Cl)-OPO_3H_2$ was used, containing about 3% of the straight-chain isomer $C_6F_{13}CH\,Cl-CH_2-OPO_3H_2$.

33 grams of this ester (0.069 mol) was dissolved with 8.28 grams sodium hydroxide (0.207 mol) in 200 ml water. The resulting solution was boiled at reflux for one hour under constant agitation. Over this period, the pH decreased from 13 to about 8–8.5 and 91.5% of the chlorine was transformed to chloride. After cooling, the solution was extracted with ether to effect separation from 0.4 grams of a neutral oil whose compositions was not elucidated and a small quantity of a sublimable solid melting at 68°–70° C which we have identified as the glycol $C_6F_{13}13\,CHOH-CH_2OH$. The remaining solution was acidified with hydrochloric acid and again extracted by ether. On evaporation of the solvent at 120° C. under 15 torrs pressure there was obtained as residue 29 grams of an oily ocher-colored solid melting at between 105° and 153° C.

A small aliquot of this product was converted to a trimethylsilyl ester by reaction with hexamethyl-disilazane and analyzed by gas chromatography combined with mass spectrometry. The following fractions were thus separated and identified in the state of the silyl derivative:

| Structure | Mol% |
|---|---|
| $C_6F_{13}-CH$ with $CH_2-O$ forming cyclic $P(=O)(OH)$ | 3.2 |
| $C_6F_{13}-\underset{CH_3}{\overset{O}{\underset{\|}{C}}}-O-P(OH)_2$ or isomers | 9.5 |
| $C_6F_{13}CH(CH_2Cl)-O-P(OH)_2$ and/or $C_6F_{13}-CHCl-CH_2O-P(OH)_2$ | 3.8 |
| $C_6F_{13}-CH(CH_2OH)-O-P(OH)_2$ | 1.8 |
| $C_6F_{13}-CHOH-CH_2O-P(OH)_2$ | 78.0 |
| Residual | 3.7 |

About 80% of the saponification product thus corresponds to fluorinated glycol monoesters having formulas I and II wherein $n=6$. Their infra-red spectra have two, free and hydrogen-bound hydroxyl bands at 3630 and 3550 cm$^{-1}$ respectively, in agreement with the preponderance of alpha monoester. This preponderance was subsequently verified by $^{31}P$ NMR (See Example 4). This principal product of saponification gives foaming aqueous solutions whose surface tensions were measured at 22° C. to be:

| Concentraton (ppm) | 50 | 250 | 1000 |
|---|---|---|---|
| Surface Tension (dynes/cm) | 37.2 | 30.4 | 20.7 |

Aqueous solutions of the mono-sodium and di-sodium salts of the same product have surface tensions at 250 ppm. concentration equal to 27.3 and 27.8 dynes/cm. respectively.

EXAMPLE 2

As a starting product a chlorinated monoester was used $C_8F_{17}$—CH(CH$_2$Cl)—OPO$_3$H$_2$ containing less than 5% of the unbranched isomer. A solution of 41.25 grams of this ester (0.0714 mol) and 10.36 grams (0.26 mol9 of sodium hydroxide in 230 ml water was refluxed under agitation.

After 3 hours, the proportion of saponified chlorine reached 87% of theory, and the heating was stopped. On cooling, a gel was obtained having pH equal to about 13. This gel was acidified with hydrochloric acid and a gelatinous precipitate separated. This was taken up in ether and finally after vacuum distillation there was recovered 35.1 grams of a cream-colored solid which was poorly crystallized and melted at between 136 and 149° C. The curve obtained by potentiometric titration by potassium hydroxide in methanol-water showed two points of inflexion corresponding respectively to the neutralization of the first and second hydrogen ions, i.e. corresponding to measurements $A_1$ of the strong acidity and $A_2$ of the total acidity; expressed in milligrams KOH per gram of sample, these were:

|  | $A_1$ | $A_2$ |
|---|---|---|
| Found for principal product of this Example | 98.8 | 198.8 |
| Calculated for $C_8F_{17}$—CHOH—CH$_2$O—PO$_3$H$_2$ | 100.1 | 200.2 |

Surface tensions at 22° C. of aqueous solutions containing 250 ppm. were found to be:

|  | dynes/cm |
|---|---|
| $C_8F_{17}$—CHOH—O—20—PO$_3$H$_2$ itself | 24.2 |
| Monosodium salt thereof | 31.7 |
| Disodium salt thereof | 41.9 |

EXAMPLE 3

The starting product of this example was a chlorinated monoester $C_{10}F_{21}$—CH(CH$_2$Cl)—OPO$_3$H$_2$ containing less than 5% of its unbranched isomer. Five grams of this ester (0.00737 mol) were treated under reflux with 22.1 ml. of aqueous normal sodium hydroxide, under constant agitation. The reaction was interrupted at the end of 3 hours. The resulting foamy solution, having pH=8.5, gelled on cooling. After acidification and extraction with ether as in Example 2, there was obtained 3.4 grams of a cream-colored crystalline solid, melting between 159° and 173° C. and dissolving in water to give solutions with a high degree of foaming.

Acidity indexes, measured as in Example 2, expressed in milligrams to KOH per gram, were as follows:

|  | $A_1$ | $A_2$ |
|---|---|---|
| Product of this example | 73.1 | 146.2 |
| Calculated as $C_{10}F_{21}$—CHOH—CH$_2$O—PO$_3$H$_2$ | 85 | 170 |

Surface tensions of 250 ppm aqueous solutions were as follows at 22° C:

|  | Dynes/cm |
|---|---|
| Crude $C_{10}F_{21}$—CHOH—CH$_2$O—PO$_3$H$_2$ | 37.4 |
| Monosodium salt thereof | 40.8 |
| Disodium salt thereof | 51.1 |

EXAMPLE 4

The starting product used was a chlorophosphate $C_{10}F_{21}$ CH(CH$_2$Cl)—OP(O)Cl$_2$ containing several percent of unbranched isomer, 10.3 grams of this product (0.0144 mol) were treated by 3.2 grams of sodium hydroxide (0.08 mol) in 96 ml. water, under constant agitation. The temperature was raised over a period of 40 minutes to the boiling point and was again maintained at reflux for 3 hours, by which time the fraction of saponified chlorine was 94.6%. The resulting solution, having a pH higher than 12 again gelled on cooling. After the same finishing steps as in Example 3, there was finally obtained 7.7 grams of crude monoester $C_{10}F_{21}$—CHOH—CH$_2$O—PO$_3$H$_2$, melting at 158°–169° C. and having acidity indexes $A_1$ - 78.0 and $A_2$ - 153.3 milligrams KOH. per gram of sample.

The 31p NMR spectrum of the product dissolved in heavy acetone CD$_3$COCD$_3$ showed a triplet at − 0.84 ppm., J=9Hz, which confirmed that the product was essentially the alpha monoester.

EXAMPLE 5

In a series of experiments the procedure of the preceding example is followed except that the aqueous solution in which the acid is taken up contains respectively trimethylamine, triethanolamine and piperidine, in each case in amount chemically equivalent to the phosphoric ester. Evaporation to dryness of the respective solutions results in surfactant powdered solid products.

EXAMPLE 6

An aqueous solution is prepared of an acid phosphate ester of this invention prepared as in Example 3. In a series of demonstrations, aliquots of this solution are mixed with aqueous solutions of respectively calcium chloride, strontium sulfate, aluminum chloride, zinc acetate and lead nitrate in amounts sufficient to cause precipitation of the corresponding calcium strontium, aluminum, zinc and lead salts of $C_{10}F_{21}$—CH(CH$_2$OH)OPO$_3$H$_2$ and $C_{10}F_{21}$-CHOHCH$_2$O—PO$_3$H$_2$. These precipitates are dried to yield powdered solids which are effective as ingredients of polishing waxes.

EXAMPLE 7

A quantity of a chlorinated monoester $C_{10}F_{21}$—CH(CH$_2$Cl)OPO$_3$H$_2$, containing less than 5% of its unbranched isomer, is treated with aqueous sodium hydroxide as in Example 3. After a saponification corresponding to about 95% of theory, a solution having pH 13 is obtained. Aliquots of this solution are acidified with hydrochloric acid to make solutions with pH equal to 11, 9, 8, 7, and 6 respectively. These solutions are all evaporated to dryness to give powdery products which can be further comminuted by grinding.

EXAMPLE 8

To an aliquot of the saponified product of the previous example there is added an amount of glauber's salt, $Na_2SO_4·10H_2O$ equal in weight to the solids contained in the product. The mixture is again evaporated to dryness to produce a solid surfactant concentrate, particularly useful as a wetting agent.

EXAMPLE 9

A solid acid product is prepared as in Example 3. This is taken up in an aqueous solution of a chemical equivalent quantity of tetramethyl ammonium hydroxide and evaporated to dryness to leave tetramethyl ammonium salts of $C_{10}F_{21}$—$CH(CH_2OH)OPO_3H_2$ and $C_{10}F_{21}$—$CHOHCH_2O$—$PO_3H_2$.

What we claim is:

1. Compounds of the formula

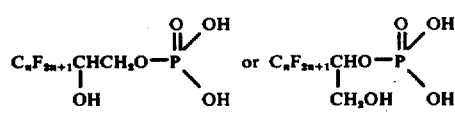

wherein $n$ is 2 to 18 and salts thereof.

2. The salts of the phosphoric acid monoesters of claim 1.

3. The alkali metal salts of the phosphoric acid monoesters of claim 1.

4. A process for the preparation of compounds of the formula

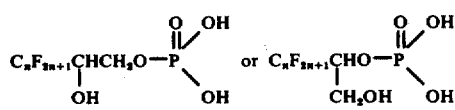

wherein $n$ is 2 to 18 which comprises hydrolyzing compounds of the formula

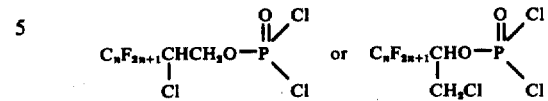

or compounds of the formula

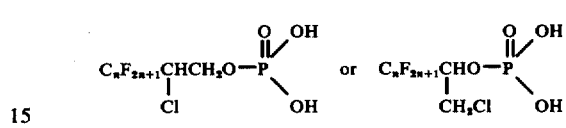

in an aqueous alkaline medium followed by acidification.

5. A process for the preparation of the phosphoric acid monoesters of claim 1 which comprises reacting the diacidic phosphoric acid or dichlorophosphoric acid monoester of the perfluoroalkylethylene chlorohydrins between $C_2$ and $C_{18}$ inclusive with a base at a temperature between $-20°$ C and $+200°$ C.

6. The process of claim 5 wherein the reaction is carried out in alkaline aqueous medium.

7. The process of claim 5 wherein the reaction is carried out in an aqueous solution of sodium or potassium hydroxide.

8. The process of claim 7 wherein the solution of the reaction product is evaporated to dryness without removal of the sodium or potassium chloride formed.

9. A process according to claim 5 in which the perfluoroalkylethylene chlorohydrin monoesters are diacidic phosphoric acid monoesters.

10. A process according to claim 5 in which the perfluoroalkylethylene chlorohydrin monoesters are dichlorophosphoric acid monoesters.

* * * * *